United States Patent [19]

Ingolia et al.

[11] Patent Number: 4,885,252

[45] Date of Patent: Dec. 5, 1989

[54] **RECOMBINANT DNA EXPRESSION VECTORS AND DNA COMPOUNDS THAT ENCODE ISOPENICILLIN N SYNTHETASE FROM *ASPERGILLUS NIDULANS***

[75] Inventors: Thomas D. Ingolia; Stephen W. Queener, both of Indianapolis; Paul L. Skatrud, Greenwood; Barbara J. Wiegel, Indianapolis, all of Ind.

[73] Assignee: Eli Lilly and Company, Indianapolis, Ind.

[21] Appl. No.: 133,760

[22] Filed: Dec. 14, 1987

Related U.S. Application Data

[63] Continuation-in-part of Ser. No. 94,345, Sep. 8, 1987, abandoned.

[51] Int. Cl.$^4$ .................. C12N 15/00; C12N 1/20; C12N 1/14; C07H 15/12

[52] U.S. Cl. .................. 435/252.3; 435/172.3; 435/183; 435/252.33; 435/254; 435/320; 536/27; 935/14; 935/27; 935/34; 935/61; 935/68; 935/72

[58] Field of Search .................. 435/70, 91, 170, 171, 435/172.3, 252.3, 254, 320, 911, 913, 925, 933, 935, 849; 536/27; 935/6, 7, 8, 9, 14, 22, 23, 24, 36, 44, 60, 61, 68, 73

[56] References Cited

U.S. PATENT DOCUMENTS 4,710,473 12/1987 Morris .................. 435/320

FOREIGN PATENT DOCUMENTS

0191221A1 8/1986 European Pat. Off. .

OTHER PUBLICATIONS

Kelly et al., 1985 *EMBO J.* 4/2/:475.
Van Solinger et al., 1985 *J. Cell. Biochem* Suppl 9c: (abstr 1576/i174.
Peñalva et al, 1985, *J. Cell. Biochem.* suppl 9c: (Abstr. 1570/, 172.
Samson, et al., Nature 318:191, 1985.
Carr, et al., Gene 48:257, 1986.
Hynes, et al., Mol. Cell, Bio. 3(8):1430, 1983.
Ramon et al., 1987, Gene 57:171.

*Primary Examiner*—Elizabeth C. Weimar
*Assistant Examiner*—Richard C. Peet
*Attorney, Agent, or Firm*—Ron K. Levy; Leroy Whitaker

[57] ABSTRACT

DNA compounds and recombinant DNA expression vectors that encode and drive expression in recombinant host cells of the isopenicillin N synthetase activity of *Aspergillus nidulans* are useful to produce isopenicillin N synthetase and to improve the yield of β-lactam-containing antibiotics from antibiotic-producing organisms. The isopenicillin N synthetase gene of *A. nidulans* can be isolated from plasmid pOGOO4, available from the Northern Regional Research Center under the accession number NRRL B-18171.

20 Claims, 4 Drawing Sheets

Figure 1
Restriction Site and Function Map of Plasmid pLC2
(7,050 bp)

Figure 2
Restriction Site and Function Map of Plasmid pOG04
(7,200 bp)

Figure 3
Restriction Site and Function Map of Plasmid pOG0216
(7,500 bp)

Figure 4
Restriction Site and Function Map of Plasmid pCZR111
(6,395 bp)

RECOMBINANT DNA EXPRESSION VECTORS AND DNA COMPOUNDS THAT ENCODE ISOPENICILLIN N SYNTHETASE FROM *ASPERGILLUS NIDULANS*

CROSS-REFERENCE TO RELATED APPLICATIONS

This application is a continuation-in-part of copending application Ser. No. 094,345, filed Sept. 8, 1987, now abandoned.

SUMMARY OF THE INVENTION

The present invention comprises a DNA sequence that encodes the isopenicillin N synthetase activity of *Aspergillus nidulans*. Isopenicillin N synthetase catalyzes the reaction in which isopenicillin N is formed from δ-(-α-aminoadipyl)-L-cysteinyl-D-valine. This reaction is a critical step in the biosynthesis of important antibiotics such as penicillins from *Aspergillus nidulans*, *Penicillium chrysogenum*, *Cephalosporium acremonium*, and *Streptomyces clavuligerus*; cephalosporins from *C. acremonium*; and 7a-methoxycephalosporins from *S. clavuligerus*.

The novel DNA sequence that encodes the isopenicillin N synthetase activity was isolated from *Aspergillus nidulans* and is useful to construct recombinant DNA expression vectors that drive expression of the activity. The present invention includes vectors that drive high-level expression of the isopenicillin N synthetase activity in *E. coli*.

The *E. coli*-produced isopenicillin N synthetase activity catalyses the reaction that forms isopenicillin N from δ-(-α-aminoadipyl)-L-cysteinyl-D-valine. Crude cell extracts from *E. coli* transformed with the *E. coli* vectors of the present invention exhibit isopenicillin N synthetase activity without any prior activation treatment. The *E. coli* vectors of the present invention thus provide an efficient means for obtaining large amounts of active isopenicillin N synthetase. Isopenicillin N synthetase is useful, not only for the production of isopenicillin N, but also for the condensation of tripeptides other than δ-(L-α- aminoadipyl)-L-cysteinyl-D-valine to form novel antibiotics.

The DNA compounds encoding isopenicillin N synthetase are readily modified to construct expression vectors that increase the efficiency and yield of antibiotic fermentations involving other organisms, such as *Aspergillus nidulans*, *Cephalosporium acremonium*, *Penicillium chrysogenum*, and *Streptomyces clavuligerus*. Although the isopenicillin N synthetase-encoding DNA of the present invention was isolated from *Aspergillus nidulans*, the present DNA compounds can be used to construct vectors that drive expression of isopenicillin N synthetase activity in a wide variety of host cells, as the *E. coli* vectors of the present invention illustrate. All organisms that produce penicillins and cephalo-sporins utilize the common precursors δ-(L-α-amino-adipyl)-L-cysteinyl-D-valine and isopenicillin N. Therefore, the isopenicillin N synthetase-encoding DNA compounds of the present invention can be used to produce vectors useful for improving efficiency and yield of fermentations involving penicillin and cephalosporin antibiotic-producing organisms of all genera.

The isopenicillin N synthetase-encoding DNA compounds of the present invention were derived from *Aspergillus nidulans* genomic DNA and were isolated in conjunction with the transcription and translation activating sequence that controls the expression of the isopenicillin N synthetase-encoding genomic DNA. The present invention comprises this novel transcription and translation activating sequence, which can be used to drive expression of genes in *A. nidulans* and related organisms.

The present invention also comprises the regulatory signals of the isopenicillin N synthetase gene that are located at the 3' end of the coding strand of the coding region of the gene. These 3' regulatory sequences encode the transcription termination and mRNA polyadenylation and processing signals of the *Aspergillus nidulans* isopenicillin N synthetase gene. The presence of these signals in the proper position (at the 3' end of the coding strand of the coding region of the gene to be expressed) in an expression vector enhances expression of the product encoded by the vector.

The following section provides a more detailed description of the present invention. For purposes of clarity and as an aid in understanding the invention, as disclosed and claimed herein, the following items are defined below.

aIPNS - isopenicillin N synthetase-encoding DNA of *Aspergillus nidulans*.

Antibiotic - a substance produced by a microorganism that, either naturally or with limited chemical modification, will inhibit the growth of or kill another microorganism or eukaryotic cell.

Antibiotic Biosynthetic Gene - a DNA segment that encodes an activity that is necessary for a reaction in the process of converting primary metabolites into antibiotics.

Antibiotic-Producing Organism - any organism, including, but not limited to, Aspergillus, Streptomyces, Bacillus, Monospora, Cephalosporium, Penicillium, and Nocardia, that either produces an antibiotic or contains genes that, if expressed, would produce an antibiotic.

Antibiotic Resistance-Conferring Gene - a DNA segment that encodes an activity that confers resistance to an antibiotic.

ApR - the ampicillin resistance-conferring gene.

Asp DNA - DNA from *Aspergillus nidulans*.

cI857 - a temperature sensitive mutant allele of the cI repressor gene of bacteriophage lambda.

Cloning - the process of incorporating a segment of DNA into a recombinant DNA cloning vector.

cos - phage λ cohesive end sequences.

Genomic Library - a set of recombinant DNA cloning vectors into which segments of DNA, which substantially represent the entire genome of a particular organism, have been cloned.

HmR - the hygromycin B resistance-conferring gene.

Hybridization - the process of annealing two homologous single-stranded DNA molecules to form a double-stranded DNA molecule, which may or may not be completely base-paired.

IPS or IPNS - Isopenicillin N synthetase; depending on context, may refer to the protein or DNA encoding the protein.

Isopenicillin N Synthetase - an enzyme, also known as cyclase, which catalyzes the formation of isopenicillin N from δ-(L-α-aminoadipyl)-L-cysteinyl-D-valine.

mRNA - messenger ribonucleic acid.

Pen DNA - DNA from *Penicillium chrysogenum*.

pIPS - isopenicillin N synthetase-encoding DNA of *Penicillium chrysogenum*.

pL or λ pL - leftward promoter of bacteriophage lambda.

Recombinant DNA Cloning Vector - any autonomously replicating or integrating agent, including, but not limited to, plasmids, comprising a DNA molecule to which one or more additional DNA molecules can be or have been added.

Recombinant DNA Expression Vector - any autonomously replicating or integrating agent, including, but not limited to, plasmids, comprising a transcription and/or translation activating sequence positioned to drive expression of a DNA segment that encodes a polypeptide or RNA of research or commercial interest.

Recombinant DNA Vector - any recombinant DNA cloning or expression vector.

Restriction Fragment - any linear DNA molecule generated by the action of one or more enzymes.

rRNA - ribosomal ribonucleic acid.

Sensitive Host Cell - a host cell that cannot grow in the presence of a given antibiotic without a DNA segment that confers resistance thereto.

TcR - the tetracycline resistance-conferring gene.

Transcription Activating Sequence - a DNA sequence such as a promoter that promotes transcription of DNA.

Transformant - a recipient host cell that has undergone transformation.

Transformation - the introduction of DNA into a recipient host cell that changes the genotype and results in a change in the recipient cell.

Translation Activating Sequence - a DNA sequence such as a ribosome-binding site-encoding sequence that, when translated into mRNA, promotes translation of mRNA into protein.

BRIEF DESCRIPTION OF THE FIGURES

The restriction site and function maps presented in FIGS. 1-4 of the accompanying drawings are approximate representations of the recombinant DNA vectors discussed herein. The spacing of restriction sites on the map is proportional to the actual spacing of the restriction sites on the vector, but observed restriction site distances may vary somewhat from calculated map distances. The restriction site information is not exhaustive; therefore, there may be more restriction sites of a given type on the vector than actually shown on the map.

FIG. 1. A restriction site and function map of plasmid pLC2.

FIG. 2. A restriction site and function map of plasmid pOG04.

FIG. 3. A restriction site and function map of plasmid pOG0216.

FIG. 4. A restriction site and function map of plasmid pCZR111.

DETAILED DESCRIPTION OF THE INVENTION

The present invention comprises DNA compounds and recombinant DNA cloning and expression vectors that encode the isopenicillin N synthetase activity of *Aspergillus nidulans*. The coding sequence of the isopenicillin N synthetase gene of *Aspergillus nidulans* can be isolated on an −2 kb HindIII-BglII restriction fragment of plasmid pOG04. This restriction fragment and coding sequence have been further characterized by DNA sequencing. The sequence of the *A. nidulans* isopenicillin N synthetase-encoding DNA is depicted below, together with a portion of the DNA that flanks the 3' end of the coding region in the *A. nidulans* genome. In the depiction, only the "sense" or coding strand of the double-stranded DNA molecule is shown, and the DNA is depicted from left to right in the 5'→3' orientation. The nucleotide sequence is numbered; the numbers appear above the DNA sequence. Immediately below each line of DNA sequence, the amino acid residue sequence of the isopenicillin N synthetase encoded by the DNA is listed from left to right in the amino-terminus→carboxyterminus direction. Each amino acid residue appears below the DNA that encodes it. The amino acid residue sequence is numbered; the numbers appear below the amino acid residue sequence.

DNA Sequence Encoding the *Aspergillus nidulans* Isopenicillin N Synthetase and Corresponding Amino Acid Sequence

```
                10              20              30              40
5'-ATG GGT TCA GTC AGC AAA GCC AAT GTT CCA AAG ATC GAT GTT TCT CCC
   MET GLY SER VAL SER LYS ALA ASN VAL PRO LYS ILE ASP VAL SER PRO
                 5              10              15

50              60              70              80              90
   CTG TTT GGA GAC GAC CAA GCA GCC AAA ATG AGA GTA GCC CAG CAA ATC
   LEU PHE GLY ASP ASP GLN ALA ALA LYS MET ARG VAL ALA GLN GLN ILE
               20              25              30

100             110             120             130             140
   GAC GCC GCT TCG CGT GAT ACT GGG TTT TTC TAC GCC GTC AAC CAT GGG
   ASP ALA ALA SER ARG ASP THR GLY PHE PHE TYR ALA VAL ASN HIS GLY
           35              40              45

150             160             170             180             190
   ATC AAT GTG CAG CGA CTC TCG CAG AAG ACC AAG GAG TTT CAT ATG TCT
   ILE ASN VAL GLN ARG LEU SER GLN LYS THR LYS GLU PHE HIS MET SER
             50              55              60

200             210             220             230             240
   ATC ACA CCT GAG GAA AAG TGG GAC CTT GCG ATT CGT GCC TAC AAC AAA
   ILE THR PRO GLU GLU LYS TRP ASP LEU ALA ILE ARG ALA TYR ASN LYS
   65              70              75              80
```

-continued
DNA Sequence Encoding the *Aspergillus nidulans* Isopenicillin N Synthetase and Corresponding Amino Acid Sequence

```
        250             260             270             280
GAG CAC CAG GAC CAA GTC CGT GCC GGA TAC TAC CTG TCC ATC CCC GGG
GLU HIS GLN ASP GLN VAL ARG ALA GLY TYR TYR LEU SER ILE PRO GLY
                85                      90                      95

290             300             310             320             330
AAA AAG GCA GTC GAG TCC TTC TGC TAC CTT AAC CCG AAC TTC ACG CCC
LYS LYS ALA VAL GLU SER PHE CYS TYR LEU ASN PRO ASN PHE THR PRO
                100                     105                     110

340             350             360             370             380
GAT CAT CCC CGT ATC CAG GCC AAG ACT CCC ACT CAC GAG GTA AAC GTG
ASP HIS PRO ARG ILE GLN ALA LYS THR PRO THR HIS GLU VAL ASN VAL
                115                     120                     125

390             400             410             420             430
TGG CCA GAC GAG ACC AAG CAC CCT GGT TTC CAA GAC TTT GCC GAG CAG
TRP PRO ASP GLU THR LYS HIS PRO GLY PHE GLN ASP PHE ALA GLU GLN
                130                     135                     140

440             450             460             470             480
TAT TAC TGG GAT GTT TTC GGT CTC TCT TCT GCA CTG CTC AAG GGC TAC
TYR TYR TRP ASP VAL PHE GLY LEU SER SER ALA LEU LEU LYS GLY TYR
145                     150                     155                     160

490             500             510             520
GCC TTG GCA TTA GGC AAA GAG GAG AAT TTC TTC GCT CGC CAC TTC AAG
ALA LEU ALA LEU GLY LYS GLU GLU ASN PHE PHE ALA ARG HIS PHE LYS
                165                     170                     175

530             540             550             560             570
CCA GAC GAT ACT CTT GCC TCG GTT GTG CTG ATC CGC TAC CCT TAC CTG
PRO ASP ASP THR LEU ALA SER VAL VAL LEU ILE ARG TYR PRO TYR LEU
                180                     185                     190

580             590             600             610             620
GAT CCC TAC CCC GAG GCT GCT ATC AAG ACG GCG GCC GAC GGC ACC AAA
ASP PRO TYR PRO GLU ALA ALA ILE LYS THR ALA ALA ASP GLY THR LYS
                195                     200                     205

630             640             650             660             670
CTG AGT TTT GAG TGG CAT GAG GAT GTA TCC CTA ATC ACT GTG CTT TAC
LEU SER PHE GLU TRP HIS GLU ASP VAL SER LEU ILE THR VAL LEU TYR
                210                     215                     220

680             690             700             710             720
CAG TCC AAC GTG CAG AAC CTG CAG GTA GAA ACT GCT GCC GGG TAT CAA
GLN SER ASN VAL GLN ASN LEU GLN VAL GLU THR ALA ALA GLY TYR GLN
225                     230                     235                     240

730             740             750             760
GAT ATC GAG GCC GAC GAT ACT GGC TAC TTG ATC AAC TGC GGC AGT TAC
ASP ILE GLU ALA ASP ASP THR GLY TYR LEU ILE ASN CYS GLY SER TYR
                245                     250                     255

770             780             790             800             810
ATG GCA CAT CTC ACA AAC AAC TAC TAT AAA GCG CCC ATC CAT CGG GTG
MET ALA HIS LEU THR ASN ASN TYR TYR LYS ALA PRO ILE HIS ARG VAL
                260                     265                     270

820             830             840             850             860
AAA TGG GTT AAT GCA GAG CGC CAG TCC CTG CCA TTC TTC GTC AAC CTG
LYS TRP VAL ASN ALA GLU ARG GLN SER LEU PRO PHE PHE VAL ASN LEU
                275                     280                     285

870             880             890             900             910
GGA TAC GAC AGC GTG ATT GAT CCA TTT GAT CCC CGA GAA CCC AAT GGC
GLY TYR ASP SER VAL ILE ASP PRO PHE ASP PRO ARG GLU PRO ASN GLY
                290                     295                     300

920             930             940             950             960
AAG TCT GAT CGG GAG CCA CTC TCC TAC GGC GAC TAT TTG CAA AAC GGG
LYS SER ASP ARG GLU PRO LEU SER TYR GLY ASP TYR LEU GLN ASN GLY
305                     310                     315                     320
```

-continued
DNA Sequence Encoding the *Aspergillus nidulans* Isopenicillin N Synthetase and Corresponding Amino Acid Sequence

```
        970         980         990         1000
CTG GTG AGT TTG ATC AAC AAG AAC GGC CAG ACC TAG AAGCGAGGGG
LEU VAL SER LEU ILE ASN LYS ASN GLY GLN THR
            325             330

1010        1020        1030        1040        1050
TGTGGAACTA GCAGATAGCA CCTGTGGACG GCGGTTACGT TGTCCTTTAG 1060        1070        1080        1090        1100
GAATTGAGAC TGAGAAGAAG CGAGTCGAGA AATTAGAGAG GCGCTACACC 1110        1120        1130        1140        1150
ATTTTAGCTA GTTTAATTCT TCTACATTTT GTTCTTTCCA CTCCACTATT 1160        1170        1180        1190        1200
CGATCGTAGC AACGGAATTG AAGCAGTTCG ATCATATACA GTGTTAAGAT 1210        1220        1230        1240        1250
CACCAGAGAA TACCCAAATT CCTCCGCGCT ATTTGTTTTC TAATTTTCTG 1260        1270        1280        1290        1300
TTACTAATGA TAACTGTGAG AACGAAACAG TAATCCCTCC CAAAAGCCAT 1310        1320        1330        1340        1350
CACCATATGG CGTGGAGAAC TGCGAGAGGG TCTCTCAGAA CGAGTCATTC 1360        1370        1380        1390        1400
GAGCTGCAGA ATTGCACAGG CCCTTTTCGC TCCACCCGCA GCGCCACGAA 1410        1420        1430        1440        1450
TCCGGTTGGC ATCGGCGCGA TGTCACCTGC AATGGAACGG CGATAGGATC 1460        1470        1480        1490        1500
TTGATGCTCA CCAGCCAATC ACAGGTTCTC CAAGAAGCAC TCGGGATCC—3'
``` wherein A is deoxyadenyl, G is deoxyguanyl, C is deoxycytidyl, T is thymidyl, ALA is an Alanine residue, ARG is an Arginine residue, ASN is an Asparagine residue, ASP is an Aspartic Acid residue, CYS is a Cysteine residue, GLN is a Glutamine residue, GLU is a Glutamic Acid residue, GLY is a Glycine residue, HIS is a Histidine residue, ILE is an Isoleucine residue, LEU is a Leucine residue, LYS is a Lysine residue, MET is a Methionine residue, PHE is a Phenylaanine residue, PRO is a Proline residue, SER is a Serine residue, THR is a Threonine residue, TRP is a Tryptophan residue, TYR is a Tyrosine residue, and VAL is a Valine residue.

Those skilled in the art will recognize that the DNA sequence depicted above is an important part of the present invention. Due to the degenerate nature of the genetic code, which results from there being more than one codon for most of the amino acid residues and stop signal, the amino acid residue sequence of isopenicillin N synthetase depicted above can be encoded by a multitude of different DNA sequences. Because these alternate DNA sequences would encode the same amino acid residue sequence of the present invention, the present invention further comprises these alternate sequences.

These IPNS-encoding sequences can be conventionally synthesized by the modified phosphotriester method using fully protected deoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. U.S.A. 75:5765. An especially preferred method of synthesizing DNA is disclosed in Hsiung et al., 1983, Nucleic Acid Research 11:3227 and Narang et al., 1980, Methods in Enzymology 68:90. In addition to the manual procedures referenced above, the DNA sequence can be synthesized using automated DNA synthesizers, such as the Systec 1450A or ABS 380A DNA Synthesizers.

In addition to the IPNS-encoding DNA sequences discussed above, there could be genetic variants of the isopenicillin N synthetase-encoding DNA of the present invention. These genetic variants represent naturally occurring genetic diversity and would share substantial DNA and amino acid residue sequence homology with the compounds of the present invention and would have similar, if not identical, activity, but would differ somewhat in nucleotide sequence from the actual compounds of the present invention. These genetic variants are equivalent to the compounds of the present invention and can be obtained by virtue of homology with the IPNS-encoding DNA sequences of the present invention.

Figure 1:
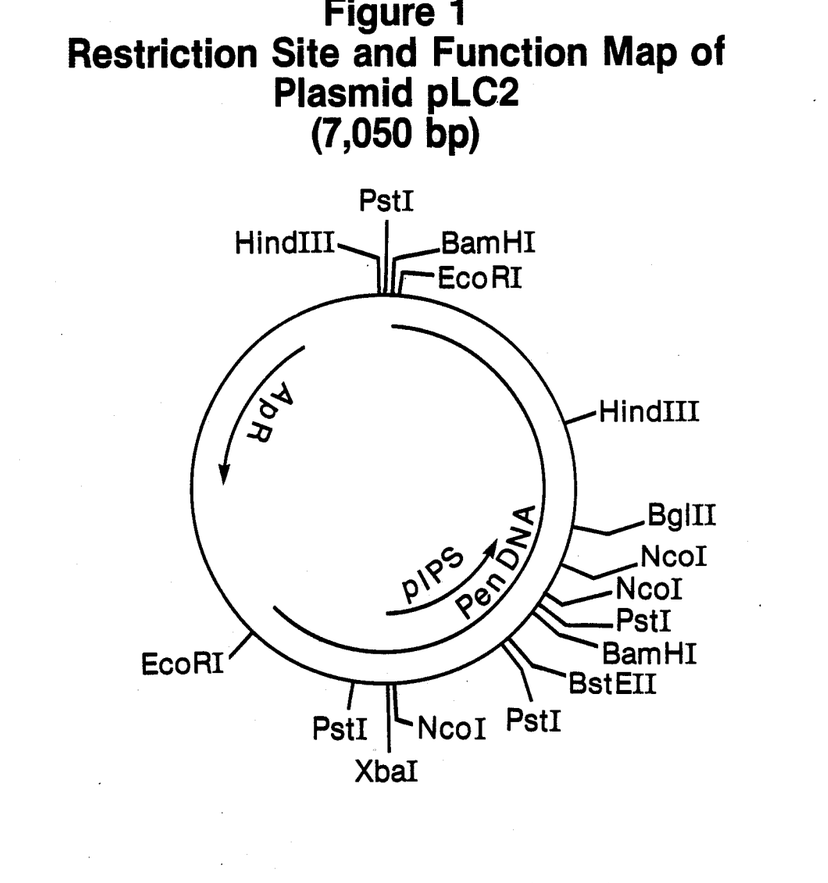
Figure 2:
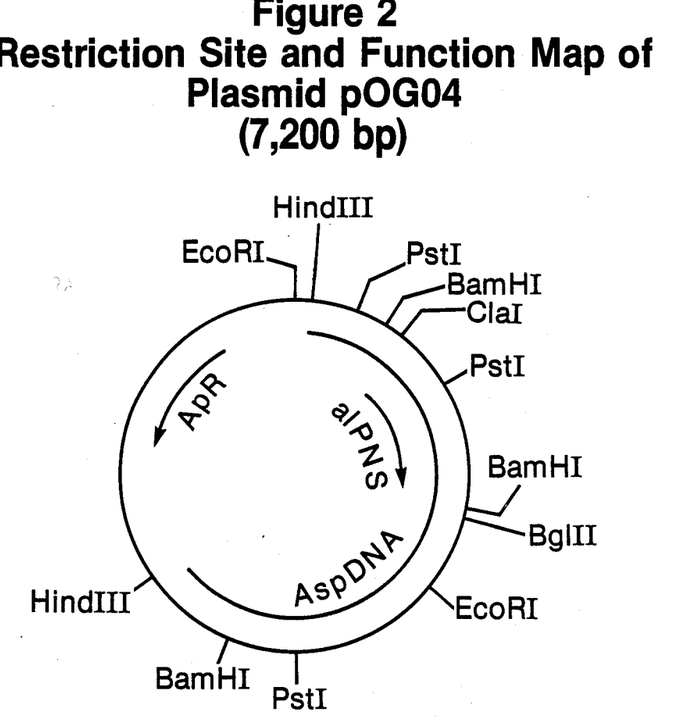

The isopenicillin N synthetase activity-encoding DNA compounds of the present invention were isolated from *Aspergillus nidulans*. A genomic library of the total genomic DNA of *A. nidulans* was constructed, and the genomic library was examined for the presence of sequences homologous to the *Penicillium chrysogenum* isopenicillin N synthetase gene encoded on plasmid pLC2, a plasmid available from the American Type Culture Collection, Rockville, MD 20852, under the accession number ATCC 53334. Plasmid pLC2, a restriction site and function map of which is presented in FIG. 1 of the accompanying drawings, is disclosed and claimed in U.S. patent application Ser. No. 801,523, filed Nov. 25, 1985, attorney docket No. X-6932. A variety of the vectors of the genomic library contained DNA homologous to the *P. chrysogenum* isopenicillin N synthetase gene, and DNA sequencing revealed that at least one of those vectors encoded the *A. nidulans* isopenicillin N synthetase. The *Aspergillus nidulans* isopenicillin N synthetase gene was then cloned into another vector to yield plasmid pOG04, which was transformed into *E. coli* K12 JM109 host cells. The *E. coli* K12 JM109/pOG04 transformants were deposited and made part of the stock culture collection of the Northern Regional Research Laboratories (NRRL), Agricultural Research Service, U.S. Department of Agriculture, Peoria, Illinois 61604, under the accession number NRRL B-18171. A restriction site and function map of plasmid pOG04 is presented in FIG. 2 of the accompanying drawings.

Figure 3:
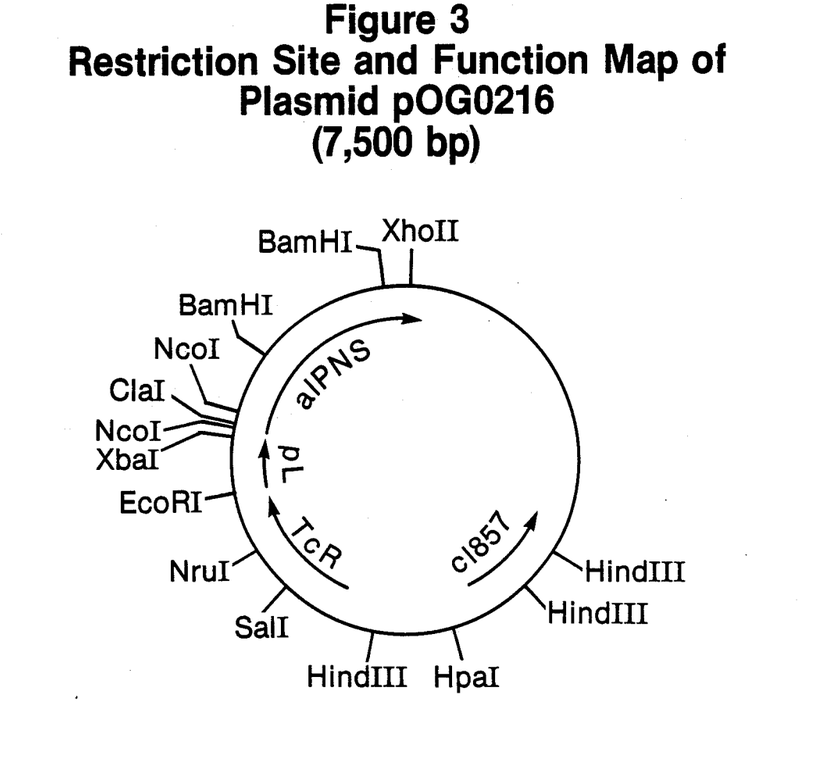

Plasmid pOG04 can be isolated from *E. coli* K12 JM109/pOG04 by the procedure described in Example 1. Useful restriction fragments can be obtained from plasmid pOG04 and include an ~4.5 kb HindIII fragment, which comprises the entire IPNS gene, and an ~1.55 kb ClaI-BglII restriction fragment, which encodes all but the amino terminus of IPNS. Plasmid pOG04 was used as starting material in the construction of a plasmid, designated pOG0216, that drives high-level expression of isopenicillin N synthetase in *E. coli*. Plasmid pOG0216 is constructed by inserting the *Aspergillus nidulans* IPNS coding sequence into a plasmid pCZR111-like expression vector that comprises the lamda pL promotor, the CI857 temperature sensitive repressor gene, a tetracycline resistance-conferring gene, and DNA sequences encoding vector replication functions. The use of the type of temperature-inducible expression system present on plasmid pCZR111 is described and disclosed in U.S. Patent Application Ser. No. 769,221, filed Aug. 26, 1985, attorney docket number X-6638, incorporated herein by reference. Essentially, at low temperature of about 30° C. the cI857 gene product represses transcription driven by the pL promoter, but when the temperature is raised to ~42° C, the cI857 gene product is inactivated and the pL promoter becomes active. Plasmid pCZR111 is available from the NRRL under the accession number NRRL B-18249. A restriction site and function map of plasmid pCZR111 is presented in FIG. 3 of the accompanying drawings.

Plasmid pOG0216 comprises the lambda pL promoter and a 2-cistron translation activating sequence positioned to drive expression of the protein-coding sequence of the *Aspergillus nidulans* isopenicillin N synthetase gene from plasmid pOG04. Two-cistron constructions are generally described in Schoner et al., 1984, Proc. Natl. Acad. Sci. 81:5403–5407 and Schoner et al., 1986, Proc. Natl. Acad. Sci. 83:8506–8510. The ~1.6 kb ClaI-BglII restriction fragment of plasmid pOG04 comprises all but about the first 36 bp of the protein-coding sequence for the isopenicillin N synthetase of *Aspergillus nidulans*. The first 36 bp of the isopenicillin N synthetase coding sequence on plasmid pOG0216 is encoded on a synthetic DNA fragment with the following sequence:

for plasmid pOG0216 is described in greater detail in Example 2.

At temperatures of about 42° C., *E. coli* K12 RV308 (NRRL B-15624) cells harboring plasmid pOG0216 express isopenicillin N synthetase at high levels, approaching ~10% of the total cell protein. Crude cell extracts from these *E. coli* K12 RV308/pOG0216 transformants are able to catalyze the conversion of δ-(L-α-aminoadipyl)-L-cysteinyl-D-valine into isopenicillin N, whereas cell extracts from *E. coli* K12 RV308 cells cannot catalyze this conversion. The method of assay for the conversion reaction is presented in Example 3.

Plasmid pOG0216 provides an efficient means of producing large amounts of isopenicillin N synthetase in *E. coli*. Because *E. coli* transformants containing plasmid pOG0216 express isopenicillin N synthetase at levels approaching 10% of total cell protein, and because culturing *E. coli* is less complex than culturing organisms that naturally produce isopenicillin N synthetase, *E. coli*/pOG0216 transformants can be used to produce recombinant isopenicillin N synthetase more efficiently and economically than non-recombinant or "natural" isopenicillin N synthetase producers. The *E. coli* K12/pOG0216 transformants of the present invention, by producing such high levels of isopenicillin N synthetase, allow for the isolation of the isopenicillin N synthetase encoded on the *Aspergillus nidulans* genome in substantially pure form.

Isopenicillin N synthetase can be used to produce isopenicillin N from 6-(L-o-aminoadipyl)-L-cysteinyl-D-valine in a cell-free system, as described in Example 3. Isopenicillin N is not only a useful antibiotic, but also is the starting material for the production of such important antibiotics as penicillin N, cephalexin, and other cephalo-sporins as described in U.S. Pat. No. 4,307,192. Another important use of isopenicillin N synthetase is for condensing tripeptides other than δ-(L-α-aminoadipyl)-L-cysteinyl-D-valine into novel β-lactam derivatives.

Cell-free extracts of penicillin-producing organisms can be used to synthesize unnatural (not produced in nature) β-lactams. The *E. coli* expression vectors of the present invention provide an inexpensive and efficient method of obtaining isopenicillin N synthetase, both in crude cell extracts and in substantially purified form, which can be used in vitro to condense tripeptides that do not naturally occur in nature to form novel antibiotics or antibiotic core structures.

Plasmid pOG0216 is especially preferred for driving expression of IPNS in *E. coli* not only because of the high expression levels achieved when using the plasmid but also because of the selectable marker present on the plasmid. Many recombinant DNA vectors encode a β-lactamase, so that cells transformed with such vectors can grow in the presence of certain β-lactam antibiotics, such as ampicillin. However, if one desires to use a cell-free extract containing IPNS for purposes of constructing β-lactams, one would not want the extract to contain β-lactamase activity. Thus, plasmid pOG0216 does not encode a β-lactamase for a selectable marker

```
    Met Gly Ser Val Ser Lys Ala Asn Val Pro Lys Ile
5'-ATG GGT TCA GTC AGC AAA GCC AAT GTT CCA AAG ATC—3'
    ||| ||| ||| ||| ||| ||| ||| ||| ||| ||| ||| |||
3'-TAC CCA AGT CAG TCG TTT CGG TTA CAA GGT TTC TAG—5'
```

The rest of the isopenicillin N synthetase coding sequence present on plasmid pOG0216 was derived directly from plasmid pOG04. A construction protocol but rather encodes the tetracycline resistance-conferring gene, the gene product of which is non-reactive with β-lactams.

The IPNS expression vectors of the present invention are not limited to a particular selectable marker. Those skilled in the art recognize that many selectable markers are suitable for use on IPNS expression vectors. Such selectable markers include genes that confer kanamycin resistance, i.e., a selectable marker on TN903, and genes that confer chloramphenicol resistance, i.e., a selectable marker on plasmids pACYC184 and pBR325.

The vectors of the present invention include vectors that drive expression of IPNS in β-lactam producing organisms. The β-lactamase gene cannot be used as a selectable marker in a β-lactam-producing microorganism. The β-lactamase gene can be present on vectors of the present invention designed for use in β-lactam-producing organisms simply because of its utility as a selectable marker in *E. coli*. Many vectors designed for β-lactam-producing organisms also are constructed so as to replicate in *E. coli* for ease of plasmid preparation. Certain β-lactam-producing organisms, such as *Cephalosporium acremonium*, are eukaryotic cells, but nevertheless, the prokaryotic β-lactamase gene derived from plasmid pBR322 seems to function in some eukaryotic host cells. See Marczynski and Jaehning, 1985, Nuc. Acids Res. 13(23):8487-8506 and Breunig et al., 1982, Gene 20:1-10. To avoid the possibility of introducing a β-lactamase gene that could possibly express in an organism transformed to obtain greater β-lactam-producing ability, the present invention also comprises vectors that utilize a selectable marker other than the β-lactamase gene, such as a chloramphenicol acetyltransferase-encoding gene.

As stated above, a β-lactamase gene cannot be used as a selectable marker in *Cephalosporium acremonium*, *Penicillium chrysogenum*, *Streptomyces clavuligerus*, or *Aspergillus nidulans*, nor do these organisms encode an endogenous β-lactamase. However, many *E. coli* strains, even those sensitive to β-lactams, do encode and express, at low levels, an endogenous β-lactamase, i.e., the *E. coli* ampC gene product. See Juarin et al., 1981, Proc. Natl. Acad. Sci. 78(8):4897-4901 and Grundström et al., 1982, Proc. Natl. Acad. Sci. 79:1111-1115. The presence of the ampC gene product in crude cell extracts of recombinant *E. coli* cells containing an IPNS expression vector could lead to degradation of β-lactams prepared using that extract. To avoid such degradation, *E. coli* K12 RV308 was subjected to mutagenesis to obtain a strain, designated *E. coli* K12 A85892, that does not express a β-lactamase activity (unless the activity is encoded on a recombinant vector present in the cell). *E. coli* K12 A85892 can be obtained from the Northern Regional Research Center under the accession number NRRL B-18096.

The search for unnatural tripeptides that will serve as substrates for isopenicillin N synthetase can be complemented by a search for mutant isopenicillin N synthetases that will accept unnatural tripeptides as substrate. The present invention provides the starting material for such a search for a mutant isopenicillin N synthetase. *E. coli* is the best host for mutational cloning experiments, and the *E. coli* expression vectors of the present invention can be readily mutated by procedures well known in the art, such as, for example, treatment with radiation (X-ray or UV) or chemical mutagens (such as ethylmethanesulfonate, nitrosoguanidine, or methyl methanesulfonate) or site-specific mutagenesis, to obtain mutant enzymes that recognize unnatural tripeptides as substrate and catalyze the condensation of those unnatural tripeptides to unnatural β-lactams.

The present invention is not limited to the particular vectors exemplified herein. The DNA compounds of the present invention encode the isopenicillin N synthetase activity of *Aspergillus nidulans* and can be used to isolate homologous DNA compounds from other Aspergillus strains that encode genetic variants of the isopenicillin N synthetase of the present invention. Consequently, the present invention comprises DNA compounds homologous to the isopenicillin N synthetase-encoding DNA on plasmids pOG04 and pOG0216 that encode isopenicillin N synthetase activity. The DNA compounds of the present invention can be used to construct expression vectors that drive expression of isopenicillin N synthetase in any host cell in which the expression vector replicates or integrates and in which the transcription and translation activating sequence used to express the isopenicillin N synthetase activity functions.

The *E. coli* expression vectors of the invention are not limited to the specific vectors exemplified herein. The present invention comprises any *E. coli* expression plasmid or vector that drives expression of isopenicillin N synthetase in *E. coli*. Thus, the present invention comprises expression vectors that drive expression of isopenicillin N synthetase and utilize a replicon functional in *E. coli*, such as, for example, a runaway replicon or a replicon from such plasmids as pBR322, pACYC184, F, ColV-K94, R1, R6-5, or R100. Nor is the present invention solely limited to plasmid vectors, for the present invention also comprises expression vectors that express isopenicillin N synthetase activity and utilize integration or viral replication to provide for replication and maintenance in the host cell.

The present invention is not limited to a particular transcription and translation activating sequence to drive expression of the isopenicillin N synthetase activity-encoding DNA. The present invention comprises the use of any transcription and translation activating sequence to express isopenicillin N synthetase in *E. coli*. Many transcription and translation activating sequences that function in *E. coli* are known and are suitable for driving expression of isopenicillin N synthetase activity in *E. coli*. Such transcription and translation activating sequences include, but are not limited to, the lpp, lac, trp, tac, λp$_L$, and λp$_R$ transcription and translation activating sequences.

In addition to the various *E. coli* replicons and transcription and translation activating sequences exemplified above, replicons and transcription and translation activating sequences from other organisms can be ligated to the present isopenicillin N synthetase encoding DNA compounds to form expression vectors that drive expression of isopenicillin N synthetase activity in host cells in which the replicon and activating sequence function. Although *E. coli* is the host best suited for isopenicillin N synthetase production and subsequent purification for in vitro use, vectors that drive expression of isopenicillin N synthetase activity in host cells other than *E. coli* are also useful, especially for purposes of increasing the β-lactam antibiotic-producing ability and efficiency of a given organism.

A variety of organisms produce -lactam antibiotics. The following Table presents a non-comprehensive list of β-lactam antibiotic-producing organisms.

TABLE I

β-Lactam Antibiotic-Producing Organisms

| Organism | Antibiotic |
|---|---|
| Agrobacterium | various β-lactams |
| Aspergillus nidulans | various β-lactams |
| Cephalosporium acremonium | penicillins and cephalosporins |
| Chromobacterium | various β-lactams |
| Gluconobacter | various β-lactams |
| Nocardia lactamdurans | cephamycin C |
| uniformis | nocardicin |
| Penicillium chrysogenum | various penicillins and other β-lactams |
| Serratia | various β-lactams |
| Streptomyces antibioticus | clavulanic acid |
| argenteolus | asparenomycin A, MM 4550, and MM 13902 |
| cattleya | thienamycin |
| chartreusis | SF 1623 and cephamycin A and B |
| clavuligerus | PA-32413-I, cephamycin C, A16886A, penicillins, cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |
| hygroscopicus | deacetoxycephalosporin C |
| lipmanii | cephamycin, penicillin N, 7-methoxycephalosporin C, A16884, MM4550, MM13902 |
| olivaceus | epithienamycin F, MM 4550, and MM 13902 |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |
| viridochromogenes | cephamycin A and B |
| wadayamensis | WS-3442-D |

Many of the foregoing β-lactam antibiotic-producing organisms are used in the pharmaceutical industry for purposes of antibiotic production. The antibiotic-producing ability of these organisms can be increased and made more efficient by increasing the intracellular concentration of rate-limiting antibiotic biosynthetic enzymes during the fermentation. The isopenicillin N synthetase activity-encoding DNA compounds of the present invention can be used to construct expression vectors. When these IPNS expression vectors are transformed into a host cell that produces a β-lactam antibiotic via an intermediate reaction involving isopenicillin N synthetase activity, the intracellular concentration of isopenicillin N synthetase activity is increased. Provided that IPNS activity is the rate-limiting factor of the β-lactam biosynthesis in the untransformed host cell, host cells containing these IPNS expression vectors produce more β-lactam antibiotic than their untransformed counterparts.

A vector that will increase the intracellular concentration of isopenicillin N synthetase activity of a given host cell into which the vector is transformed requires the following elements: (1) an isopenicillin N synthetase activity-encoding DNA compound; (2) a transcription and translation activating sequences that not only functions in the host cell to be transformed, but also is positioned in the correct orientation and position to drive expression of the isopenicillin N synthetase activity-encoding DNA; and (3) replication or integration functions that provide for maintenance of the vector in the host cell. The frequency of integration of a DNA vector often is quite dependent on activities encoded by the host cell; however, it is often observed that certain DNA sequences (i.e., sequences from viruses and phages that facilitate integration and sequences homologous to the host's genomic DNA), when present on a recombinant DNA vector facilitate integration. Of course, an IPNS expression vector could also comprise an antibiotic resistance-conferring gene or some other element that provides a means of selecting for host cells which contain the vector, but such selectable elements may be neither necessary nor desired when the vector integrates into the chromosomal DNA of the host cell.

A variety of the plasmids of the present invention are useful for increasing the intracellular concentration of isopenicillin N synthetase activity in a β-lactam antibiotic-producing cell. Plasmid pOG04 comprises the intact isopenicillin N synthetase gene of *Aspergillus nidulans*, so transformation of *A. nidulans* via chromosomal integration of plasmid pOG04 leads to increased copy number of the isopenicillin N synthetase gene and thus leads to increased intracellular concentration of the enzyme. European Patent Publication number 0191221A1, incorporated herein by reference, describes various transformation protocols that can be used to transform Aspergillus with a recombinant DNA vector. The *Aspergillus nidulans* isopenicillin N synthetase gene also is believed to function in *Cephalosporium acremonium* and *Penicillium chrysogenum*. Consequently, transformation of *P. chrysogenum* or *C. acremonium* via chromosomal integration of plasmid pOG04 leads to increased copy number of the isopenicillin N synthetase gene and thus leads to increased intracellular concentration of the enzyme.

However, the *Aspergillus nidulans* IPNS coding sequence of the invention can also be put under the control of transcription and translation activating sequences derived from Penicillium and Cephalosporium to construct a recombinant gene especially for use in these organisms. U.S. patent application Ser. No. 06/895,008, filed Aug. 8, 1986, attorney docket No. X-6722B, incorporated herein by reference, discloses the transcription and translation activating sequences of the *C. acremonium* IPNS gene, which can be fused to the *A. nidulans* IPNS coding sequence of the present invention to create a recombinant IPNS gene that drives expression (when incorporated into an expression vector and the vector introduced into Cephalosporium) of the *A. nidulans* IPNS in Cephalosporium. Likewise, U.S. patent application Ser. No. 06/801,523, filed Nov. 25, 1985, incorporated herein by reference, discloses the transcription and translation activating sequences of the *P. chrysogenum* IPNS gene, which can be used as described above to construct Penicillium vectors that drive expression of *A. nidulans* IPNS.

The present invention results from the cloning of an intact, functional, *Asperqillus nidulans* DNA sequence that encodes not only the amino acid sequence of isopenicillin N synthetase but also the transcription and translation activating sequence necessary to drive expression of isopenicillin N synthetase in *A. nidulans*. Likewise, the isopenicillin N synthetase gene of the present invention comprises the sequences located downstream of the coding region that are responsible for terminating transcription and for providing the mRNA polyadenylation and processing signals. These 5' and 3' regulatory elements comprise an important aspect of the present invention.

Because plasmid pOG04 comprises ~0.45 kb of the genomic DNA that was located upstream of the isopenicillin N synthetase-encoding DNA in the *Aspergillus nidulans* genome, plasmid pOG04 necessarily comprises the transcription and translation activating sequence of the *A. nidulans* isopenicillin N synthetase gene. Most transcription and translation activating sequences are encoded upstream of the DNA to be activated, although some ribosomal RNA-encoding DNA sequences are activated by transcription activating sequences that are not located upstream of the coding region. "Upstream," in the present context, refers to DNA in the 5' direction from the 5' end of the coding strand of the isopenicillin N synthetase-encoding DNA.

The *Aspergillus nidulans* transcription and translation activating sequence encoded on plasmid pOG04 is correctly positioned to drive expression of the isopenicillin N synthetase activity-encoding DNA. In the construction of plasmid pOG04, no deletions or insertions affecting the transcription and translation activating sequence were introduced in the DNA flanking the 5' end of the coding strand of the isopenicillin N synthetase activity-encoding DNA. Because the *Aspergillus nidulans* transcription and translation activating sequence located on plasmid pOG04 can be used to drive expression of a wide variety of DNA sequences, the activating sequence comprises an important part of the present invention. The activating sequence of the *A. nidulans* isopenicillin N synthetase gene can be isolated on the ~450 bp HindIII-ClaI restriction fragment located immediately upstream of and adjacent to the isopenicillin N synthetase activity-encoding DNA on plasmid pOG04. The ClaI site encodes amino acid residues 12 and 13 of the isopenicillin N synthetase protein, so the amino terminal coding region of the isopenicillin N synthetase is also contained on this HindIII-ClaI fragment. Any restriction fragment that comprises the aforementioned ~450 bp HindIII-ClaI restriction fragment necessarily comprises the *A. nidulans* transcription and translation activating sequence of the present invention.

The DNA sequence of the *Aspergillus nidulans* transcription and translation activating sequence encoded on plasmid pOG04 is presented below. This sequence can be chemically synthesized or isolated from plasmid pOG04. To clarify how the activating sequence is oriented in plasmid pOG04, the restriction fragment is illustrated with a single-stranded DNA overlap characteristic of restriction enzyme HindIII and the translation initiation codon is included.

DNA Sequence
of the *Aspergillus nidulans*
Transcription and Translation Activating Sequence
Encoded on Plasmid pOGO4

```
5'-AGCT TCGTTATGAT CATTTCCCAA TATTCTCTCG CTTAGGGCTG ACGTAGTCCA
     |||||||||| |||||||||| |||||||||| |||||||||| ||||||||||
3'-AGCAATACTA GTAAAGGGTT ATAAGAGAGC GAATCCCGAC TGCATCAGGT

TTCCTACTCA TCAAATTGTG GTACGAGCCA AGCCCTCTAT TCCTGGCGGG
    |||||||||| |||||||||| |||||||||| |||||||||| ||||||||||
    AAGGATGAGT AGTTTAACAC CATGCTCGGT TCGGGAGATA AGGACCGCCC

GCTATTGCTG CAGTGTCTTA CGCTGATTCA ATTTCTGCAG GGTAATGGTT
    |||||||||| |||||||||| |||||||||| |||||||||| ||||||||||
    CGATAACGAC GTCACAGAAT GCGACTAAGT TAAAGACGTC CCATTACCAA

TTAGGCGTCA CCCGACGAAG GCCGCCATGA CTATACTTGT CTACAGCCCC
    |||||||||| |||||||||| |||||||||| |||||||||| ||||||||||
    AATCCGCAGT GGGCTGCTTC CGGCGGTACT GATATGAACA GATGTCGGGG

TCGTACTTTT GCGACGAGTG TGGTCGGCTC GATGTCCAAG CCAGTCCTAC
    |||||||||| |||||||||| |||||||||| |||||||||| ||||||||||
    AGCATGAAAA CGCTGCTCAC ACCAGCCGAG CTACAGGTTC GGTCAGGATG

CCGGTCGCTT ATTTGCTTGG AGACTTGCGC GCAGACGGGA AAATAAATAA
    |||||||||| |||||||||| |||||||||| |||||||||| ||||||||||
    GGCCAGCGAA TAAACGAACC TCTGAACGCG CGTCTGCCCT TTTATTTATT

ACCCTGATGG AAATTCGCAG AAACGTCTGT TCTTCGCCGG CAATTCCTAC
    |||||||||| |||||||||| |||||||||| |||||||||| ||||||||||
    TGGGACTACC TTTAAGCGTC TTTGCAGACA AGAAGCGGCC GTTAAGGATG

CCATTAACCT ACACAAACCA GTCCAAGCCT TGGGGATCCT TCCGTTACCA
    |||||||||| |||||||||| |||||||||| |||||||||| ||||||||||
    GGTAATTGGA TGTGTTTGGT CAGGTTCGGA ACCCCTAGGA AGGCAATGGT

CCGCTTCTTC ATCAGTCTCA ACTGCTTGCC CTCATTCATA—3'
    |||||||||| |||||||||| |||||||||| ||||||||||
    GGCGAAGAAG TAGTCAGAGT TGACGAACGG GAGTAAGTAT TAC—5'
                                              ↑—→beginning of
```
isopenicillin N synthetase coding region. "TAC" is complementary to the 5'-ATG—3' that encodes the amino-terminal methionyl residue of isopenicillin N synthetase.

The *Aspergillus nidulans* transcription and translation activating sequence can be used to drive expression of any DNA sequence in *A. nidulans* and other Aspergillus species. The transcriptional promoter from the *Aspergillus nidulans* isopenicillin N synthetase gene can be fused to protein coding regions in several useful ways. For example, the majority of the 5' noncoding information can be isolated on an ~400 bp HindIII-BamHI fragment from pOG04. The remaining ~55 bp of 5' noncoding information before the 5'-ATG translation initiation codon can be appended through use of a synthetic linker, essentially as described in Example 2. The synthetic linker can incorporate useful restriction sites at the translation initiation site, such as NdeI or NcoI, to facilitate fusion of the *A. nidulans* promoter to the protein coding region of interest. The protein coding region can be similarly adapted to contain compatible ends for convenient ligation using strategies which will be different for different protein coding regions, but an exemplary strategy is outlined in Example 2, which describes the protocol for fusing the *A. nidulans* isopenicillin N synthetase protein-coding region to the *E. coli* transcriptional promoter and translation activating sequence on plasmid pCZR111.

Similar strategies allow the *A. nidulans* isopenicillin N synthetase protein coding region to be joined to transcriptional promoters and translation activating sequences from any organism of interest. For example, a transcriptional promoter from the organism of interest can be reconstructed so that the 5'-ATG translation initiation site is nested within an NcoI restriction site, 5-CCATGG-3'. An *A. nidulans* isopenicillin N synthetase protein coding region containing an NcoI restriction site at the translation initiation site, as taught in Example 2, can then be simply joined to the promoter from the organism of interest to produce a hybrid gene that will drive expression of the *A. nidulans* isopenicillin N synthetase in any organism in which the activating sequence functions. The flanking ends of the hybrid gene can be similarly adapted to allow insertion into a vector suitable for the organism of interest.

Plasmid pOG04 also comprises the 3' regulatory sequences of the *Aspergillus nidulans* isopenicillin N synthetase gene. Usually, the sequences responsible for transcription termination, mRNA polyadenylation, and mRNA processing are encoded within the region ~500 bp downstream of the stop codon of the coding region of a gene. Therefore, the ~0.65 kb HincII-BamHI restriction fragment that comprises the isopenicillin N synthetase carboxy-terminal-encoding DNA and downstream sequences also comprises the transcription termination and mRNA polyadenylation and processing signals of the *A. nidulans* isopenicillin N synthetase gene.

The transcription termination sequence in plasmid pOG04 can be appended to other recombinant gene constructions to facilitate transcription termination in those gene constructs. For example, a HincII restriction site (located at about the codons for amino acid residues 286 and 287 of the *A. nidulans* isopenicillin N synthetase) is convenient for isolating the transcription termination sequences, both because the HincII cleavage site is near the translation termination site (translation terminates after amino acid residue 331) and because HincII cleavage produces flush ends that facilitate linkage to various gene constructs. A BamHI restriction enzyme recognition site located about 510 bp downstream of the translation termination site provides a convenient distal or downstream end, allowing the transcription terminator to be isolated on an ~650 bp HincII-BamHI restriction fragment from plasmid pOG04.

Expression of a given DNA sequence on a recombinant DNA expression vector can be enhanced by placing a transcription termination and mRNA polyadenylation and processing signal at the 3' end of the coding strand of the coding region to be expressed. The present invention provides a transcription termination and mRNA polyadenylation and processing signal that can be used for the purposes of increasing expression of any gene product from a recombinant DNA vector in Aspergillus and related host cells.

The present invention provides the coding sequence for the isopenicillin N synthetase gene of *Aspergillus nidulans* and provides a number of expression vectors that drive expression of that gene in host cells such as *E. coli*. Production of isopenicillin N synthetase in *E. coli* allows for high-level expression and easy isolation of the enzyme so that the enzyme can be used to catalyze the condensation of novel tripeptides into novel antibiotic core structures in vitro. Transformation of *A. nidulans*, Cephalosporium acremonium, Penicillium chrysogenum, and other β-lactam antibiotic-producing host cells with expression vectors of the present invention that drive expression of isopenicillin N synthetase in the host cell of interest leads to higher levels of isopenicillin N synthetase and thus leads to higher levels of antibiotic in the transformed cell.

The following Examples are provided to further illustrate and exemplify the present invention but are in no way intended to limit the scope of the present invention.

EXAMPLE 1

Culture of *E. coli* K12 JM109/pOG04 and Isolation of Plasmid pOG04

A. Culture of *E. coli* K12 JM109/pOG04

A lyophil of *E. coli* K12 JM109/pOG04 is obtained from the Northern Regional Research Laboratories, Peoria, Ill. 61604, under the accession number NRRL B-18171. The lyophil can be directly used as the "culture" in the process described below.

One liter of L-broth (10 g tryptone, 10 g NaCl, and 5 g yeast extract per liter) containing 50 μg/ml ampicillin was inoculated with a culture of *E. coli* K12 JM109/pOG04 and incubated with aeration at 37° C. until the optical density at 590 nm (O.D.$_{590}$) was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

B. Isolation of Plasmid pOG04

The culture prepared in Example 1A was centrifuged in a Sorvall GSA rotor (DuPont Co., Instrument Products, Biomedical Division, Newtown, Conn. 06470) at 6000 rpm for 5 minutes at 4° C. The resulting supernatant was discarded, and the cell pellet was washed in 40 ml of TES buffer (10 mM Tris-HCl, pH=7.5; 10 mM NaCl; and 1 mM EDTA) and then repelleted. The supernatant was again discarded, and the cell pellet was frozen in a dry ice-ethanol bath and then thawed. The thawed cell pellet was resuspended in 10 ml of a solution of 25% sucrose and 50 mM EDTA. About 1 ml of a 5 mg/ml lysozyme solution; 3 ml of 0.25 M EDTA, pH=8.0; and 100 μl of 10 mg/ml RNAse A, were added to and mixed with the solution, which was then incubated on ice for 15 minutes. Three ml of lysing solution (prepared by mixing 3 ml of 10% Triton-X 100;

75 ml of 0.25 M EDTA, pH=8.0; 15 ml of 1 M Tris-HCl, pH=8.0; and 7 ml of water) were added to the lysozyme-treated cells, mixed, and the resulting solution incubated on ice for another 15 minutes. The lysed cells were frozen in a dry ice-ethanol bath and then thawed.

The cellular debris was removed from the solution by centrifugation at 25,000 rpm for 40 minutes in an SW27 rotor (Beckman, 7360 N. Lincoln Ave., Lincolnwood, Ill. 60646) and by extraction with buffered phenol. About 30.44 g of CsCl and ~1 ml of a 5 mg/ml ethidium bromide solution were added to the solution; then, the volume was adjusted to 40 ml and decanted into a VTi50 ultra-centrifuge tube (Beckman). The tube was sealed, and the solution was centrifuged in a VTi50 rotor at 42,000 rpm for ~16 hours. The resulting plasmid band, visualized with ultraviolet light, was isolated and then placed in a Ti75 tube (volume adjustments were made using TES containing 0.761 g/ml CsCl) and rotor (Beckman) and centrifuged at 50,000 rpm for 16 hours. The plasmid band was again isolated, extracted with salt-saturated isopropanol to remove the ethidium bromide, and diluted 1:3 with TES buffer. Two volumes of ethanol were then added to the solution, which was then incubated overnight at −20° C. The plasmid DNA was pelleted by centrifuging the solution in an SS34 rotor (Sorvall, DuPont Co., Newton, Conn. 06470) for 15 minutes at 10,000 rpm.

The ~1 mg of plasmid pOG04 DNA obtained by this procedure was suspended in 1 ml of TE buffer (10 mM Tris-HCl, pH=8.0, and 1 mM EDTA) and stored at −20° C. A restriction site and function map of plasmid pOG04 is presented in FIG. 2 of the accompanying drawings.

EXAMPLE 2
Construction of Plasmid pOG0216

Plasmid pOG0216 was constructed by ligating together the following four DNA fragments: an ~1.6 kb ClaI-BglII restriction fragment from plasmid pOG04 DNA that contains all but the IPNS amino-terminus-encoding portion of the *Aspergillus nidulans* IPNS coding sequence; an NcoI-ClaI double-stranded DNA linker that reconstructs the coding sequence for the amino terminus of *Aspergillus nidulans* IPNS; an ~5.3 kb EcoRI-BamHI restriction fragment from plasmid DNA of a pCZR111-derivative that contains the DNA sequences coding for the cI857 repressor, the plasmid origin of replication, and the tetracycline resistance-conferring gene; and an ~500 bp EcoRI-NcoI restriction fragment from plasmid DNA of the aforementioned pCZR111 derivative expression vector. This pCZR111 derivative differs from the parent plasmid pCZR111 only in the translation activating sequence and downstream protein-coding sequence. One skilled in the art will recognize that different plasmids can share common DNA sequences encoding promoters, translation activating sequences, origins of replication, and antibiotic resistance-conferring genes. It is often matters of convenience rather than design that dictate choices for sources of DNA sequences, such as which plasmids are prepared and ready for use. To facilitate description, construction of plasmid pOG0216 is described using plasmid pCZR111 DNA as the source for the DNA sequences encoding the λpL promoter, the plasmid origin of replication, the cI857 gene, and the tetracycline resistance-conferring gene; plasmid pOG04 as the source plasmid for all but the amino terminus-encoding portion of *Aspergillus nidulans* IPNS coding sequence; and a double-stranded synthetic DNA linker as the source of DNA coding for the two cistron translation activating sequence as well as the amino terminus-encoding portion of the *Aspergillus nidulans* IPNS coding sequence.

A. Culture of *E. coli* K12 RV308/pCZR111 and Isolation of Plasmid pCZR111

Figure 4:
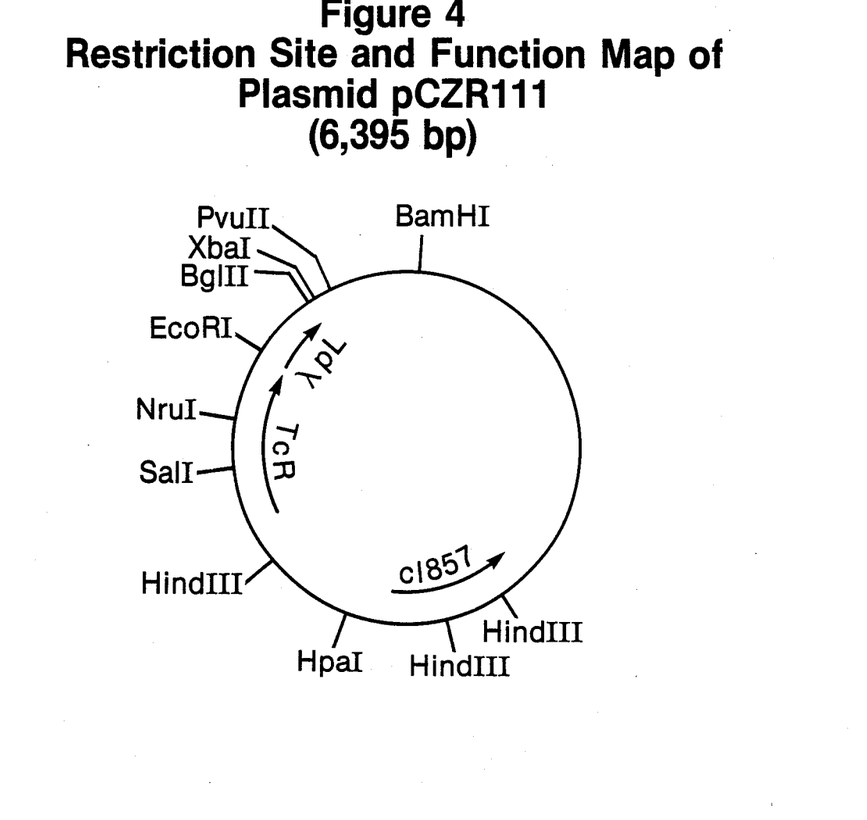

A lyophil of *E. coli* K12 RV308/pCZR111 is obtained from the NRRL under the accession number NRRL B-18249. The lyophil is reconstituted in L broth; the resulting culture is used to prepare plasmid pCZR111 DNA in substantial accordance with the procedure described in Example 1. However, because the selectable marker on plasmid pCZR111 is the tetracycline resistance-conferring gene, the culture medium contains 10 μg/ml tetracycline and no ampicillin. In addition, the culture is incubated at 25°–30° C., instead of 37° C., to prevent transcription from the lambda pL promoter. About 1 mg of plasmid pCZR111 DNA is obtained by this procedure and dissolved in ~1 ml of 0.1 X TE buffer. A restriction site and function map of plasmid pCZR111 is presented in FIG. 4 of the accompanying drawings. B. Isolation of the ~5.8 kb XbaI-BamHI Restriction Fragment of Plasmid pCZR111

Approximately 25 μg (in 25 ~1 of 0.1 X TE buffer) of the plasmid pCZR111 DNA prepared in Example 2A are added to and mixed with 40 ~1 of 10X XbaI buffer (500 mM Tris-HCl, pH =8.0; 500 mM NaCl; and 100 mM MgCl$_2$), 335 ~1 of water, 2 ~1 (50 units) of restriction enzyme BamHI, and 3 ~1 (60 units) of restriction enzyme XbaI. Unless otherwise noted, restriction enzymes referred to herein can be obtained from New England Biolabs, 32 Tozer Road, Beverly, Mass. 01915. Unit definitions herein correspond to the particular manufacturer's unit definitions. The resulting reaction is incubated at 37° C. for 90 minutes. The DNA is concentrated by precipitation with ethanol and NaOAc and collected by centrifugation. The DNA pellet is resuspended in ~80 μl of water and ~20 ~1 of 5X loading buffer (70% glycerol, 50 mM EDTA, and 1 mg/mL bromphenol blue) and electrophoresed on an ~1.0% agarose gel until the desired ~5.8 kb XbaI-BamHI restriction fragment is clearly separated from the other digestion product, an ~600 bp XbaI-BamHI restriction fragment. Visualization of the electrophoresed DNA is accomplished by staining the gel in a dilute solution of ethidium bromide ~1 μg/μl) and exposing the gel to long-wave UV light.

The desired fragment is located, excised from the gel, and the ~5.8 kb XbaI-BamHI restriction fragment recovered using a D-Gel=DNA electroeluter (Epigene, Box 4817, Baltimore, MD, 21211) in substantial accordance with the manufacturer's directions. Two volumes of ethanol are added to the DNA, which is recovered from the eluter in 500 μl of 1 M NaCl. The resulting solution is incubated at −20° C. for ~5 hours, then centrifuged at 15,000 rpm for 20 minutes. The DNA pellet is rinsed first with 70% ethanol and then with 100% ethanol, dried, and resuspended in 20 μl of 0.1 X TE buffer. This solution constitutes about 2 μg of the desired ~5.8 kb XbaI-BamHI restriction fragment and is stored at −20° C.

C. Preparation of Plasmid pOG04 DNA from *E. coli* K12 GM48

The ClaI restriction site located at about the codons for amino acid residues 13 and 14 of the *Aspergillus nidulans* isopenicillin N synthetase coding sequence is methylated in dam+*E. coli* strains, because the "G" residue preceding the ClaI recognition sequence produces the 5'-GATC-3' sequence that is methylated at the "A" residue by the dam gene product. Because ClaI restriction enzyme will not cleave when either "A" residue in the recognition sequence is methylated, it was necessary to prepare plasmid pOG04 DNA from a dam mutant strain of *E. coli*, such as *E. coli* K12 GM48, to isolate the ~1.6 kb ClaI-BglII restriction fragment of plasmid pOG04 for use in the construction of plasmid pOG0216.

*E. coli* K12 GM48 is obtained from the Northern Regional Research Laboratories under accession number NRRL B-15725. The lyophil of *E. coli* K12 GM48 cells is used to inoculate ~100 ml of L broth, and the culture is incubated at 37° C. until the absorbance at 600 nm is about 0.5–0.7. A variety of procedures exist for preparing *E. coli* cells competent for transformation. One such procedure is described below. The cells are centrifuged at 5,000Xg for 5 minutes, washed in 50 ml of sterile cold 10 mM NaCl, and centrifuged again. The cells are then gently resuspended in 2–5 ml of sterile, cold 75 mM CaClz and are then competent for transformation. About ~100 mg of the plasmid pOG04 DNA prepared in Example 1A were added to 200 ~1 of the *E. coli* GM48 cells, and the mixture was incubated on ice for 1 hour. The mixture was then incubated at 42° C. for 2 minutes, then diluted into 2 ml of L broth and incubated for 1 hour at 37° C. without shaking. Aliquots were plated on L agar plates containing 100 μg/ml ampicillin, and the plates were incubated at 37° C. overnight. Individual ampicillin-resistant colonies were grown, and plasmid pOG04 DNA was prepared from the *E. coli* GM48/pOG04 transformants in substantial accordance with the procedure described in Example 1.

D. Isolation of the ~1.6 kb ClaI-BglII Restriction Fragment of Plasmid pOG04 that Encodes Isopenicillin N Synthetase Approximately 25 μg (in 25 ~1 of TE buffer) of the plasmid pOG04 DNA prepared in Example 2C were dissolved in 10 μl of 10X ClaI buffer (0.5 M NaCl; 0.06 M Tris-HCl, pH=7.9; 0.06 M MgClz; 1 mg/ml BSA) and 60 μl of H2O. About 5 μl (50 units) of restriction enzyme ClaI were added to the solution of plasmid pOG04 DNA, and the resulting reaction was incubated at 37° C. for two hours. Then, about 5 μl (50 units) of restriction enzyme BglII were added to the reaction mixture and the resulting reaction was incubated at 37° C. for an additional 2 hours. The ClaI-BglII-digested DNA obtained was loaded onto a 1% agarose gel, and the desired ~1.6 kb ClaI-BglII restriction fragment was isolated, purified, and prepared for ligation. Approximately 2 μg of the desired fragment was obtained, suspended in 20 ~1 of TE buffer, and stored at −20° C.

E. Construction of an *XbaI-ClaI* Linker

Two complementary single-stranded DNA fragments can be synthesized on an automated DNA synthesizer and subsequently annealed to form a double-stranded fragment. Many DNA synthesizing instruments are known in the art and are suitable for making the fragments. One such instrument is an ABS 380A DNA Synthesizer (Applied Biosystems, Inc. 850 Lincoln Centre Dr., Foster City, CA 94404). In addition, the fragment can also be conventionally prepared in substantial accordance with the procedures of Itauura et al., 1977, Science, 198:1056 and Crea et al., 1978, Proc. Natl. Acad. Sci. U.S.A. 75:5765.

The following linkers are synthesized:

```
5'-CTAGAGGGTATTAATAATGTATCGCGATTTAAATAAGGAGGAATAAACCATGGGTTCAG-
                                          TCAGCAAAGCCAATGTTCCAAAGAT—3'

5'-CGATCTTTGGAACATTGGCTTTGCTGACTGAACCCATGGTTTATTCCTCCTTATTTAAA-
                                          TCGCGATACATTATTAATACCCT—3'
```

About 100 pmols of each single-stranded DNA fragment are kinased in separate 50 μl reactions containing the single-stranded DNA fragment, 5 μl of 10X ligase buffer, 5 μl of 5 mM ATP, water to adjust the final reaction volume to 50 μl and 1 μl (~10 Richardson units) of T4 polynucleotide kinase. The reactions are incubated at 37° C. for 30 minutes. The two reactions are then combined, and the resulting 100 μl of reaction mixture are heated to 90° C. and allowed to cool slowly to 4° C. to optimize annealing of the complementary single-stranded fragments. The resulting double-stranded DNA fragment, the linker, is:

```
XbaI overlap
5'-CTAGAGGGTATTAATAATGTATCGCGATTTAAATAAGGAGGAATAAACCATGGGTTCAG-
   |||||||||||||||||||||||||||||||||||||||||||||||||||||||
       TCCCATAATTATTACATAGCGCTAAATTTATTCCTCCTTATTTGGTACCCAAGTC- TCAGCAAAGCCAATGTTCCAAAGAT—3'
                               |||||||||||||||||||||||||
                               AGTCGTTTCGGTTACAAGGTTTCTAGC—5'
                                                        ClaI overlap
```

This linker joins the XbaI end of the pCZR111-derived fragment to the ClaI end of the plasmid pOG04-derived fragment, reconstructs the coding sequence for the amino terminus of *Aspergillus nidulans* isopenicillin N synthetase, and also encodes the translation activating DNA sequence.

F. Final Construction of Plasmid pOG0216

One μl of the ~5.8 kb XbaI-BamHI restriction fragment of plasmid pCZR111, 1 μl of the ~1.6 kb ClaIBglII restriction fragment of plasmid pOG04, and ~1μl (μl pmole) of the annealed synthetic linker are ligated to form plasmid pOG0216. The total reaction volume is 20 μl and contains the DNA fragments, 2 μl of 10 X ligase buffer (0.5 M Tris-HCl, pH =7.5, 100 μM MgCl₂), 2 μl of 5 mM ATP, 1 μl of a 6 μg/μl BSA solution, 9 μl of water, and 1 μl (1 Weiss unit) of T4 DNA ligase (Boehringer-Mannheim Biochemicals (BMM), P.O. Box 50816, Indianapolis, Ind. 46250). The reaction is incubated ~18 hours at 15° C. The ligated DNA constitutes the desired plasmid pOG0216. A restriction site and function map of plasmid pOGO216 is presented in FIG. 3 of the accompanying drawings.

EXAMPLE 3

Construction of E. coli K12 RV308/pOGO216 and Assay of E. coli-Produced Isopenicillin N Synthetase

A. Construction of E. coli K12 RV308/pOGO216

E. coli K12 RV308 cells competent for transformation can be prepared as follows. A 50 ml culture of E. coli K12 RV308 (NRRL B-15624) in L-broth is grown to an $O.D._{590}$ of ~0.5 absorbance units. The culture is chilled on ice for ten minutes, and the cells are collected by centrifugation. The cell pellet is resuspended in 25 ml of cold 100 mM CaCl₂ and incubated on ice for 25 minutes. The cells are once again pelleted by centrifugation, and the pellet is resuspended in 2.5 ml of cold 100 mM CaCl₂ and incubated on ice overnight.

Two hundred μl of this cell suspension are mixed with the ligated DNA prepared in Example 2F and then incubated on ice for 20 minutes. The cells are collected by centrifugation, resuspended in μl ml of L broth, and then incubated at 30° C. for one hour. Aliquots of the cell mixture are plated on L-agar (L-broth with 15 g/L agar) plates containing 10 μg/ml tetracycline, and the plates are incubated at 30° C. E. coli K12 RV308/pOGO216 transformants were verified by selection for tetracycline resistance and by restriction enzyme analysis of the plasmid DNA of the transformants. Plasmid DNA was obtained from the E. coli K12 RV308/pOGO216 transformants for restriction enzyme analysis in substantial accordance with the teaching of Example 1B, but on a smaller scale, and the CsCl-gradient steps were omitted.

B. Culture of E. coli K12 RV308/pOGO216 for Expression of Isopenicillin N Synthetase Activity Several isolates of the E. coli K12 RV308/pOGO216 transformants were individually inoculated into 5 ml aliquots of L broth containing 10 μg/ml tetracycline, and the cultures were incubated in an air-shaker incubator at 30° C. until the $O.D._{590}$ was ~0.2 absorbance units. The cultures were then transferred to a 42° C. air-shaker incubator and incubated at 42° C. for ~6 hours.

After the six-hour, 42° C. incubation, one ml of each culture was collected, and the cells were pelleted by centrifugation. The cell pellets were individually washed with 1 ml of 10 mM NaCl and then resuspended in 1.0 ml of IPNS extraction buffer (0.05 M Tris-HCl, pH=8.0; 0.01 M KCl; and 0.01 M MgS04) The cells were sonicated by six, five-second bursts of sonication delivered by a Sonifier Cell Disruptor, Model W185, Heat Systems-Ultrasonics, Inc., Plainview, Long Island, NY, using the micro tip. The time between bursts of sonication was 60 seconds, and the mixture was kept in an ice-ethanol bath during the procedure. After sonication, the cell mixture was centrifuged to remove debris and then used directly in the assay.

C. Assay for Isopenicillin N Synthetase Activity

The following assay procedure is derived from the procedure of Shen et al., 1984, J. of Antibiotics 37(9): 1044-1048. The isopenicillin N synthetase assay reaction was carried out in a total volume of 500 μl. To start the reaction, 1.0 ml of a solution of 1.4 mM δ-(L-α-aminoadipyl)-L-cysteinyl-D-valine and 3.75 mM DTT was allowed to react at room temperature for 30-60 minutes to reduce any dimeric tripeptide to the monomeric form. Fifty μl of each of the following stock solutions were aliquoted into each assay tube (sterile, glass, disposable 13×100 mm tubes): 500 mM Tris-HCl, pH=7.4; 100 mM KCl; 100 mM MgSO₄; 2.0 mM FeSO₄; and 6.7 mM ascorbic acid. Next, varying amounts of extract, diluted with water to a volume of 150 μl, were added. About 100 μl aliquots of the tripeptide solution were then added to each tube; the addition of the tripeptide starts the reaction. Each tube was vortexed upon addition of the substrate. The reaction mixture vessels were then placed in a gyrotory shaker bath at 250 rpm, with an incubation temperature of 25° C. The reaction time was 45 minutes.

After 45 minutes of reaction, 2 samples of 100 μl each were withdrawn and dispensed into wells in the bioassay plates, and 100 units of penicillinase A were added to the remainder of the sample. The penicillinase A is obtained from Riker's Laboratories, Inc.; the enzyme is sold in vials of 100,000 units, which are rehydrated to 5.0 mls with H₂O. Five μl (100 units) of the rehydrated penicillinase A were added to the remainder of each reaction mixture, allowed to react for 5 minutes at room temperature, and then 100 μl of each penicillinase A-treated extract was dispensed into the wells of a bioassay plate. This penicillinase A treatment is done to check that the zones on the bioassay plate are due to the presence of a penicillin rather than a cephalosporin or other contaminant.

The penicillin N standard curve was prepared by adding 0.5, 1.0, 2.0, 5.0, 10.0, and 20.0 μg of penicillin N to bioassay wells. The penicillinase A activity was also checked by adding 5 μl of the enzyme preparation to ~200 μl of 0.2 μg/ml penicillin N.

The bioassay plates were composed of K131 nutrient agar, which is prepared by dissolving 30.5 g BBL Antibiotic Medium #11 (Becton Dickinson & Company Cockeysville, Md.) in 1 liter of deionized water, bringing the solution to a boil, cooling to 70° C., and then autoclaving 35 minutes at 121° C. and 15 psi. The plates were seeded with 4 ml of a fresh overnight culture of Micrococcus luteus (ATCC 9341) per 700 ml of agar. The M. luteus was grown in K544 nutrient broth, which is composed of: Difco peptone, 5.0 g; Difco yeast extract, 1.5 g; sodium chloride, 3.5 g; dipotassium phosphate (anhydrous), 3.7 g; monopotassium phosphate, 1.3 g; Difco beef extract, 1.5 g, in 1 liter of deionized water—the solution is brought to a boil, cooled to 25° C., adjusted to a pH=7.0 with 1 N HCl or 1 N NaOH, and then autoclaved for 20 minutes at 121° C. and 15 psi before use. The seeded agar was dispensed into 100×15 mm plates, at 15 mls of seeded agar per plate. The wells were prepared by applying suction using a disposable 15 ml pipette; each well was 10 mm in diameter.

After the plates were prepared and the samples dispensed into the wells, the plates were placed in a 37° C. incubator for 18 hours. The assay results were determined by measuring the diameter of the cleared areas around each sample well, which result from the *M. luteus* being unable to grow when a penicillin is present.

The results of the assay demonstrate that the *E. coli* K12 RV308/pOG0216 transformants express isopenicillin N synthetase activity.

We claim:

1. An isolated DNA compound that comprises DNA that encodes isopenicillin N synthetase from Aspergillus.

2. The DNA compound of claim 1 that comprises DNA that encodes the amino acid residue sequence:

```
H2N— MET GLY SER VAL SER LYS ALA ASN VAL PRO LYS ILE ASP VAL SER PRO
      LEU PHE GLY ASP ASP GLN ALA ALA LYS MET ARG VAL ALA GLN GLN ILE
      ASP ALA ALA SER ARG ASP THR GLY PHE PHE TYR ALA VAL ASN HIS GLY
      ILE ASN VAL GLN ARG LEU SER GLN LYS THR LYS GLU PHE HIS MET SER
      ILE THR PRO GLU GLU LYS TRP ASP LEU ALA ILE ARG ALA TYR ASN LYS
      GLU HIS GLN ASP GLN VAL ARG ALA GLY TYR TYR LEU SER ILE PRO GLY
      LYS LYS ALA VAL GLU SER PHE CYS TYR LEU ASN PRO ASN PHE THR PRO
      ASP HIS PRO ARG ILE GLN ALA LYS THR PRO THR HIS GLU VAL ASN VAL
      TRP PRO ASP GLU THR LYS HIS PRO GLY PHE GLN ASP PHE ALA GLU GLN
      TYR TYR TRP ASP VAL PHE GLY LEU SER SER ALA LEU LEU LYS GLY TYR
      ALA LEU ALA LEU GLY LYS GLU GLU ASN PHE PHE ALA ARG HIS PHE LYS
      PRO ASP ASP THR LEU ALA SER VAL VAL LEU ILE ARG TYR PRO TYR LEU
      ASP PRO TYR PRO GLU ALA ALA ILE LYS THR ALA ALA ASP GLY THR LYS
      LEU SER PHE GLU TRP HIS GLU ASP VAL SER LEU ILE THR VAL LEU TYR
      GLN SER ASN VAL GLN ASN LEU GLN VAL GLU THR ALA ALA GLY TYR GLN
      ASP ILE GLU ALA ASP ASP THR GLY TYR LEU ILE ASN CYS GLY SER TYR
      MET ALA HIS LEU THR ASN ASN TYR TYR LYS ALA PRO ILE HIS ARG VAL
      LYS TRP VAL ASN ALA GLU ARG GLN SER LEU PRO PHE PHE VAL ASN LEU
      GLY TYR ASP SER VAL ILE ASP PRO PHE ASP PRO ARG GLU PRO ASN GLY
      LYS SER ASP ARG GLU PRO LEU SER TYR GLY ASP TYR LEU GLN ASN GLY
      LEU VAL SER LEU ILE ASN LYS ASN GLY GLN THR—COOH
``` wherein ALA is an Alanine residue, ARG is an Arginine residue, ASN is an Asparagine residue, ASP is an Aspartic Acid residue, -COOH is the carboxy-terminus, CYS is a Cysteine residue, GLN is a Glutamine residue, GLU is a Glutamic Acid residue, GLY is a Glycine residue, HIS is a Histidine residue, H2N- is the amino terminus, ILE is an Isoleucine residue, LEU is Leucine residue, LYS is a Lysine residue, MET is a Methionine residue, PHE is Phenylalanine residue, PRO is a Proline residue, SER is a Serine residue, THR is a Threonine residue, TRP is a Tryptophan residue, TYR is a Tyrosine residue, and VAL is a Valine residue.

3. The DNA compound of claim 2 that comprises the DNA sequence:

wherein A is deoxyadenyl, G is deoxyguanyl, C is deoxycytidyl, and T is thymidyl.

4. The DNA compound of claim 1 selected from the group consisting of the ~4.5 kb HindIII restriction fragment of plasmid pOG04 and the ~2 kb HindIII-BglII restriction fragment of plasmid pOGO4.

5. The DNA compound of claim 1 that is a plasmid.

6. The plasmid of claim 5 that is plasmid pOGO4.

7. The plasmid of claim 5 that is plasmid pOGO216.

8. A recombinant DNA host cell transformed with a recombinant DNA vector that encodes isopenicillin N synthetase from *Aspergillus nidulans*.

9. The host cell of claim 8 that is *E. coli*.

10. The host cell of claim 9 that is *E. coli* K12 JM109/pOGO4.

11. The host cell of claim 9 that is *E. coli* K12 RV308/pOGO216.

12. The host cell of claim 8 that is *Aspergillus*.

13. The host cell of claim 8 that is *Penicillium*.

14. The host cell of claim 8 that is *Cephalosporium*.

15. An isolated DNA compound that comprises the transcription and translation activating sequence of the isopenicillin N synthetase gene of *Aspergillus nidulans*.

16. The DNA compound of claim 15 that comprises ~0.45 kb HindIII-ClaI restriction fragment of plasmid 17. The DNA compound of claim 15 that comprises the DNA sequence:

```
5'- ATG GGT TCA GTC AGC AAA GCC AAT GTT CCA AAG ATC GAT GTT TCT CCC
    CTG TTT GGA GAC GAC CAA GCA GCC AAA ATG AGA GTA GCC CAG CAA ATC
    GAC GCC GCT TCG CGT GAT ACT GGG TTT TTC TAC GCC GTC AAC CAT GGG
    ATC ATT GTG CAG CGA CTC TCG CAG AAG ACC AAG GAG TTT CAT ATG TCT
    ATC ACA CCT GAG GAA AAG TGG GAC CTT GCG ATT CGT GCC TAC AAC AAA
    GAG CAC CAG GAC CAA GTC CGT GCC GGA TAC TAC CTG TCC ATC CCC GGG
    AAA AAG GCA GTC GAG TCC TTC TGC TAC CTT AAC CCG AAC TTC ACG CCC
    GAT CAT CCC CGT ATC CAG GCC AAG ACT CCC ACT CAC GAG GTA AAC GTG
    TGG CCA GAC GAG ACC AAG CAC CCT GGT TTC CAA GAC TTT GCC GAG CAG
    TAT TAC TGG GAT GTT TTC GGT CTC TCT TCT GCA CTG CTC AAG GGC TAC
    GCC TTG GCA TTA GGC AAA GAG GAG AAT TTC TTC GCT CGC CAC TTC AAG
    CCA GAC GAT ACT CTT GCC TCG GTT GTG CTG ATC CGC TAC CCT TAC CTG
    GAT CCC TAC CCC GAG GCT GCT ATC AAG ACG GCG GCC GAC GGC ACC AAA
    CTG AGT TTT GAG TGG CAT GAG GAT GTA TCC CTA ATC ACT GTG CTT TAC
    CAG TCC AAC GTG CAG AAC CTG CAG GTA GAA ACT GCT GCC GGG TAT CAA
    GAT ATC GAG GCC GAC GAT ACT GGC TAC TTG ATC AAC TGC GGC AGT TAC
    ATG GCA CAT CTC ACA AAC AAC TAC TAT AAA GCG CCC ATC CAT CGG GTG
    AAA TGG GTT AAT GCA GAG CGC CAG TCC CTG CCA TTC TTC GTC AAC CTG
    GGA TAC GAC AGC GTG ATT GAT CCA TTT GAT CCC CGA GAA CCC AAT GGC
    AAG TCT GAT CGG GAG CCA CTC TCC TAC GGC GAC TAT TTG CAA AAC GGG
    CTG GTG AGT TTG ATC AAC AAG AAC GGC CAG AAC-3'
```

```
5'-AGCT TCGTTATGAT CATTTCCCAA TATTCTCTCG CTTAGGGCTG ACGTAGTCCA
     |||||||||| |||||||||| |||||||||| |||||||||| ||||||||||
3'-AGCAATACTA GTAAAGGGTT ATAAGAGAGC GAATCCCGAC TGCATCAGGT

TTCCTACTCA TCAAATTGTG GTACGAGCCA AGCCCTCTAT TCCTGGCGGG
   |||||||||| |||||||||| |||||||||| |||||||||| ||||||||||
   AAGGATGAGT AGTTTAACAC CATGCTCGGT TCGGGAGATA AGGACCGCCC

GCTATTGCTG CAGTGTCTTA CGCTGATTCA ATTTCTGCAG GGTAATGGTT
   |||||||||| |||||||||| |||||||||| |||||||||| ||||||||||
   CGATAACGAC GTCACAGAAT GCGACTAAGT TAAAGACGTC CCATTACCAA

TTAGGCGTCA CCCGACGAAG GCCGCCATGA CTATACTTGT CTACAGCCCC
   |||||||||| |||||||||| |||||||||| |||||||||| ||||||||||
   AATCCGCAGT GGGCTGCTTC CGGCGGTACT GATATGAACA GATGTCGGGG

TCGTACTTTT GCGACGAGTG TGGTCGGCTC GATGTCCAAG CCAGTCCTAC
   |||||||||| |||||||||| |||||||||| |||||||||| ||||||||||
   AGCATGAAAA CGCTGCTCAC ACCAGCCGAG CTACAGGTTC GGTCAGGATG

CCGGTCGCTT ATTTGCTTGG AGACTTGCGC GCAGACGGGA AAATAAATAA
   |||||||||| |||||||||| |||||||||| |||||||||| ||||||||||
   GGCCAGCGAA TAAACGAACC TCTGAACGCG CGTCTGCCCT TTTATTTATT

ACCCTGATGG AAATTCGCAG AAACGTCTGT TCTTCGCCGG CAATTCCTAC
   |||||||||| |||||||||| |||||||||| |||||||||| ||||||||||
   TGGGACTACC TTTAAGCGTC TTTGCAGACA AGAAGCGGCC GTTAAGGATG

CCATTAACCT ACACAAACCA GTCCAAGCCT TGGGGATCCT TCCGTTACCA
   |||||||||| |||||||||| |||||||||| |||||||||| ||||||||||
   GGTAATTGGA TGTGTTTGGT CAGGTTCGGA ACCCCTAGGA AGGCAATGGT

CCGCTTCTTC ATCAGTCTCA ACTGCTTGCC CTCATTCATA-3'
   |||||||||| |||||||||| |||||||||| ||||||||||
   GGCGAAGAAG TAGTCAGAGT TGACGAACGG GAGTAAGTAT TAC-5'
``` wherein A is deoxyadenyl, G is deoxyguanyl, C is deoxycytidyl, and T is thymidyl.

18. A DNA compound that comprises the transcription termination and polyadenylation signals of the isopenicillin N synthetase gene of *Aspergillus nidulans*.

19. The DNA compound of claim 18 that is the ~0.65 kb HincII-BamHI restriction fragment of plasmid pOGO4.

20. The DNA compound of claim 18 that comprises the DNA sequence:

```
                                        5'-TAG AAG CGA GGG GTG
TGG AAC TAG CAG ATA GCA CCT GTG GAC GGC GGT TAC GTT GTC CTT TAG
GAA TTG AGA CTG AGA AGA AGC GAG TCG AGA AAT TAG AGA GGC GCT ACA
CCA TTT TAG CTA GTT TAA TTC TTC TAC ATT TTG TTC TTT CCA CTC CAC
TAT TCG ATC GTA GCA ACG GAA TTG AAG CAG TTC GAT CAT ATA CAG TGT
TAA GAT CAC CAG AGA ATA CCC AAA TTC CTC CGC GCT ATT TGT TTT CTA
ATT TTC TGT TAC TAA TGA TAA CTG TGA GAA CGA AAC AGT AAT CCC TCC
CAA AAG CCA TCA CCA TAT GGC GTG GAG AAC TGC GAG AGG GTC TCT CAG
AAC GAG TCA TTC GAG CTG CAG AAT TGC ACA GGC CCT TTT CGC TCC ACC
CGC AGC GCC ACG AAT CCG GTT GGC ATC GGC GCG ATG TCA CCT GCA ATG
GAA CGG CGA TAG GAT CTT GAT GCT CAC CAG CCA ATC ACA GGT TCT CCA
AGA AGC ACT CGG GAT CC-3'
``` wherein A is deoxyadenyl, G is deoxyguanyl, C is deoxycytidyl, and T is thymidyl.

* * * * *